United States Patent
Chang et al.

(10) Patent No.: US 10,660,853 B2
(45) Date of Patent: May 26, 2020

(54) METHOD FOR PREPARING LIPOSOME FROZEN POWDER CAPABLE OF EFFICIENTLY RETAINING ITS BILAYER STRUCTURE

(71) Applicant: SEOUL NATIONAL UNIVERSITY R&DB FOUNDATION, Seoul (KR)

(72) Inventors: Pahn Shick Chang, Seoul (KR); Kyung Min Park, Seoul (KR); Eun Hye Yang, Incheon (KR); Ho Sup Jung, Incheon (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 46 days.

(21) Appl. No.: 15/760,894

(22) PCT Filed: Sep. 13, 2016

(86) PCT No.: PCT/KR2016/010387
§ 371 (c)(1),
(2) Date: Mar. 16, 2018

(87) PCT Pub. No.: WO2017/048082
PCT Pub. Date: Mar. 23, 2017

(65) Prior Publication Data
US 2018/0256499 A1   Sep. 13, 2018

(30) Foreign Application Priority Data
Sep. 18, 2015 (KR) .......................... 10-2015-0132128

(51) Int. Cl.
*A61K 9/127* (2006.01)
*A61K 9/19* (2006.01)
*A61K 47/26* (2006.01)

(52) U.S. Cl.
CPC ............ *A61K 9/127* (2013.01); *A61K 9/1277* (2013.01); *A61K 9/19* (2013.01); *A61K 47/26* (2013.01)

(58) Field of Classification Search
CPC ...... A61K 9/127; A61K 47/26; A61K 9/1277; A61K 9/19
See application file for complete search history.

(56) References Cited

U.S. PATENT DOCUMENTS 2,066,302 A * 12/1936 Reichel .................. C07K 16/06
159/47.1
2,728,673 A * 12/1955 Mouton ................. C12G 3/005
426/384

(Continued)

FOREIGN PATENT DOCUMENTS

KR    10-2010-0136096 A    12/2010

OTHER PUBLICATIONS

Wang, T., et al in Colloids and Surfaces B: Biointgerfaces, vol. 79, pp. 254-261, 2010.*

*Primary Examiner* — Gollamudi S Kishore
(74) *Attorney, Agent, or Firm* — Vorys, Sater, Seymour & Pease LLP; Mih Suhn Koh

(57) ABSTRACT

Disclosed are a method of preparing liposomes using a mixed solvent of ethyl acetate and n-hexane for dissolving phospholipids, and a method of preparing a liposome frozen powder by putting a container including liposomes in a container filled with isopropyl alcohol, ethanol and/or methanol, followed by lyophilization, which methods are useful in food industry for no use of toxic chloroform. Disclosed also is adding the produced container including liposomes to a container filled with isopropyl alcohol, ethanol and/or methanol, followed by lyophilization, thus advantageously preventing deterioration in stability of liposome (Continued)

A. CP

B. CP-LMF particles, as well as being almost completely returned to the original state.

4 Claims, 13 Drawing Sheets

(56) References Cited

U.S. PATENT DOCUMENTS

| | | | | |
|---|---|---|---|---|
| 4,963,362 | A | * | 10/1990 | Rahman ................ A61K 9/127 264/4.1 |
| 5,407,921 | A | | 4/1995 | Katsuragi et al. |
| 2002/0041895 | A1 | * | 4/2002 | Gregoriadis ........... A61K 9/127 424/450 |
| 2007/0248541 | A1 | * | 10/2007 | Tagawa ................ A61K 9/127 424/9.1 |
| 2009/0053302 | A1 | * | 2/2009 | Boulikas .............. A61K 9/1075 424/450 |
| 2010/0196482 | A1 | | 8/2010 | Radovic-Moreno et al. |
| 2013/0156845 | A1 | * | 6/2013 | Manoharan ........... C12N 15/111 424/450 |
| 2014/0335157 | A1 | * | 11/2014 | Tange ................... C07C 323/25 424/450 |

* cited by examiner

|  | Chloroform | n-Hexane | Ethyl acetate | Acetone | Isopropyl alcohol |
|---|---|---|---|---|---|
| Polarity | 4.1 | 0 | 4.4 | 5.1 | 3.9 |
| Solubility in water | 0.815 | 0.001 | 8.7 | 100 | 100 |
| Viscosity | 0.57 | 0.33 | 0.45 | 0.32 | 2.30 |
| Lecithin solubility | soluble | soluble | low soluble | low soluble | low soluble |
| Vapor pressure | 25.90 | 17.60 | 9.73 | 30.60 | 6.02 |
FIG. 1
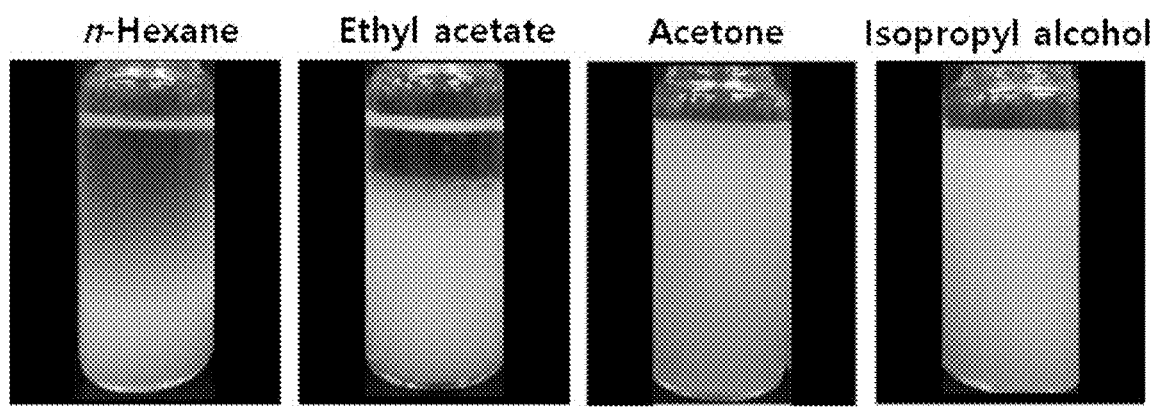
FIG. 2
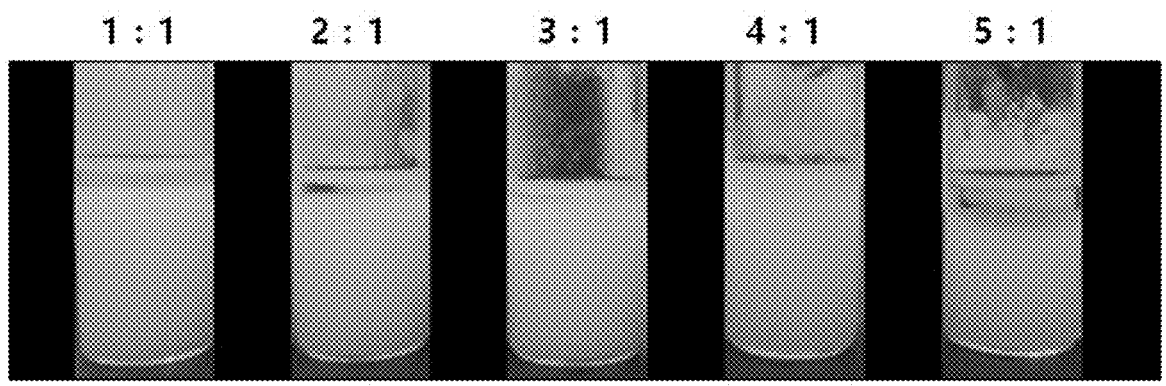
FIG. 3

A

B

METHOD FOR PREPARING LIPOSOME FROZEN POWDER CAPABLE OF EFFICIENTLY RETAINING ITS BILAYER STRUCTURE

TECHNICAL FIELD

The present invention relates to a method of preparing a liposome frozen powder capable of efficiently retaining its bilayer structure, and more particularly to a method of preparing a liposome frozen powder characterized in that a container including liposomes is put in a container including one or more selected from isopropyl alcohol, ethanol and methanol, followed by lyophilization.

BACKGROUND ART

Nano-encapsulation, which is one form of nanotechnology, is a method of protecting effective ingredients from the exterior environment and increasing bioavailability. In particular, as nano-carriers, liposomes using natural food ingredients are prepared using phospholipids which are constituent components of the human body.

Liposomes have advantages of having high biocompatibility in the human body, of possibly loading both liposoluble and water-soluble physiologically active substances, increasing permeability of cell membrane phospholipids, and enabling biodegradation in the human body. In addition, liposomes are considered to be highly available as a carrier in drug delivery systems because they can decrease toxicity of loaded drugs and protect active drugs from intrinsic factors such as heat, light and enzymes.

Liposomes are highly available owing to these advantages, but have a drawback of causing chemical decomposition or physical change during manufacture or storage. Chemical decomposition results from oxidation or hydrolysis of phospholipids, and physical change includes agglomeration and cohesion of liposome particles in an aqueous solution, leakage of effective ingredients or the like. Accordingly, there is a need for methods capable of stably storing liposomes while protecting the same from these factors.

One recently actively researched method of powderizing liposomes is lyophilization, which can improve safety of liposomes when stored for a long time.

Lyophilization is a drying method which involves freezing a solution-phase sample and allowing the sample to stand under a reduced pressure to remove moisture from the sample by sublimation and has been variably used for samples containing unstable ingredients including biomaterials. Lyophilization is a method which can improve safety and long-term storage stability of active ingredients and has advantages of easily storing, transferring and handling active ingredients. Lyophilization is applicable to the production of agricultural products, chemicals and various foods such as herbs, and is also utilized to improve safety of liposomes.

Lyophilization is currently used as a method of powderizing liposomes for two reasons. First, since moisture is removed at a low temperature, hydrolysis of phospholipids can be prevented when water is removed from an aqueous liposome solution. Second, since mobility of molecules in a solid phase is decreased, physical and chemical decomposition can be reduced.

Conventionally researched liposome powderization methods can improve storage stability of liposomes, but have drawbacks of low flowability and workability. Accordingly, in order for liposomes to be applied to functional health foods, research on novel formulations that are suitable for the liposomes is needed and powderized nanoliposomes should be dispersed again in water upon ingestion.

DISCLOSURE

Technical Problem

Conventional methods of preparing and storing liposomes have the following disadvantages.

First, in general, phospholipids, which are dissolved in an organic solvent such as chloroform or cyclohexane, are used. For this reason, there have been limitations in using liposomes in the food industry due to the toxicity of organic solvents. Most thin film methods used for mass-production of liposomes use chloroform. However, disadvantageously, chloroform, cyclohexane and the like are not allowed to be used in the food industry because they are not registered in the Food Additive Code.

Second, liposomes have a problem of low safety because particle size thereof is increased when dispersed in water. For this reason, a great deal of research had been conducted in order to improve physical and chemical stability of colloidal liposomes. A representative method to improve stability is lyophilization.

Lyophilization, which lengthens the storage period of liposomes and protects ingredients vulnerable to heat, has been variably researched. However, it is known that, in the process of lyophilization of liposomes, deterioration in stability of liposome particles such as destruction of liposome structure and leakage of active ingredients occurs.

The structure of liposomes should be maintained in order for them to be stably re-dispersed. In this case, factors affecting the structure are the size and distribution of ice crystals. As the time taken to pass the zone of maximum ice crystal formation in the process of freezing a liposome solution decreases, more small ice crystals are created and are uniformly distributed, but when the time taken to pass the zone of maximum ice crystal formation increases, ice crystals are large in size, less in number and are non-uniformly distributed, which finally causes breakage of the liposome bilayer structure.

In addition, when liposomes are powderized by lyophilization and then dissolved in an aqueous solution, since the liposome structure is changed, dispersibility is low and heating is required. That is, complete powderization of liposomes through lyophilization needs to be improved.

It is an object of the present invention to more widely use liposomes in the food industry by changing the solvent used for preparation of the liposomes to a safe ingredient, and develop and easily utilize a lyophilization powderization process that can improve stability of the liposomes.

Technical Solution

In accordance with the present invention, the above and other objects can be accomplished by the provision of a method of preparing a liposome frozen powder including putting a container including liposomes in a container filled with one or more selected from isopropyl alcohol, ethanol and methanol, followed by lyophilization.

Preferably, the liposomes may be produced by adding a cryoprotectant.

Preferably, the cryoprotectant may include one or more selected from trehalose and sucrose.

Preferably, the liposomes may be produced by a process including mixing an organic solvent, in which phospholipid is dissolved, with distilled water, in which trehalose is dissolved, to produce inverted micelles (a), and mixing a solution containing the inverted micelles with distilled water, in which sucrose is dissolved, to prepare a double emulsion (b).

Preferably, the liposomes may include one or more selected from a compound, a microorganism, a protein and an enzyme. In this case, the compound may be a pharmaceutical active ingredient or a functional health ingredient.

Advantageous Effects

The method according to the present invention has an advantage of being useful for the food industry, because a solution of phospholipids in a mixed solvent of ethyl acetate and n-hexane is used, unlike conventional methods using toxic chloroform.

In addition, the present invention involves putting a container including liposomes in a container filled with one or more selected from isopropyl alcohol, ethanol and methanol, followed by lyophilization, thereby preventing deterioration in stability of liposome particles such as destruction of liposome structure and leakage of the active ingredient in the process of lyophilization.

In addition, when the liposome frozen powder, which has been lyophilized in accordance with the method of the present invention, is dissolved again in an aqueous solution, upon use, it can be returned to the almost original state.

DESCRIPTION OF DRAWINGS

The above and other objects, features and other advantages of the present invention will be more clearly understood from the following detailed description taken in conjunction with the accompanying drawings, in which:

FIG. 1 shows results showing comparison in chemical properties between solvents registered in the Food Additive Code, and chloroform;

FIG. 2 shows inverted micelles produced using, as a solvent, n-hexane, ethyl acetate, acetone and isopropyl alcohol;

FIG. 3 shows inverted micelles produced using a mixed solvent of ethyl acetate and n-hexane in different mix ratios of 1:1, 2:1, 3:1, 4:1, and 5:1;

BEST MODE

Figure 4:
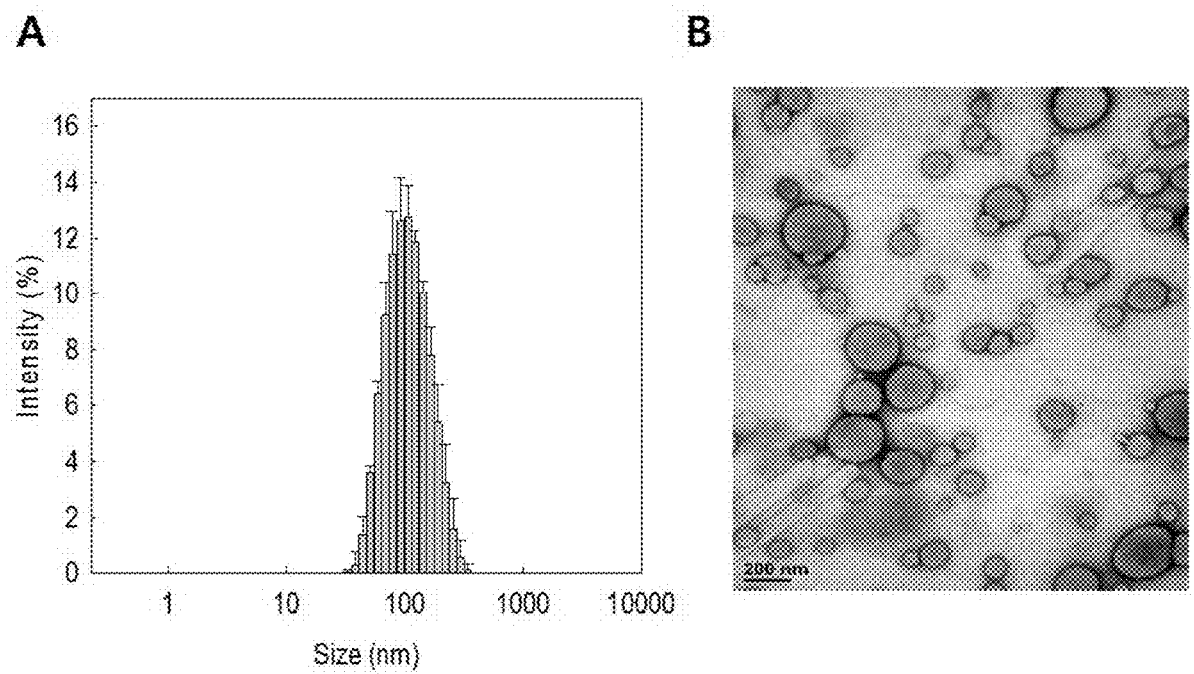
FIG. 4A is a size distribution (DLS) graph of liposomes produced using a mixed solvent of ethyl acetate and n-hexane in a ratio of 4:1
FIG. 4B is a TEM image of the liposomes.

In an attempt to accomplish the object, a first embodiment of the present invention is directed to a method of preparing liposomes including producing inverted micelles and then forming a double emulsion, wherein the inverted micelles are produced using phospholipids dissolved or suspended in a mixed solvent of ethyl acetate and n-hexane.

With regard to the method of preparing liposomes according to the present invention, the mixed solvent of ethyl acetate and n-hexane is used as a solvent for dissolving phospholipids. The experiments of the present invention showed that when liposomes are prepared by dissolving phospholipids in a mixed solvent of ethyl acetate and n-hexane, the structure of inverted micelles can be well maintained. At this time, a mix ratio of ethyl acetate to n-hexane is preferably 3:1 to 5:1 on a volume basis. The reason for this is that results of preparing liposomes using a mixed solvent of ethyl acetate and n-hexane in different mix ratios in the present invention showed that the structure of inverted micelles could be well maintained in a mix ratio of 3:1 to 5:1.

Meanwhile, with regard to the method of preparing liposomes according to the present invention, the phospholipid is for example lecithin. Phospholipid refers to a complex lipid that contains phosphoric acid ester in its molecule, and includes lecithin as well as, cephalin, sphingomyelin, cardiolipin, phosphoinositide, acetal phosphate or the like.

Meanwhile, with regard to the method of preparing liposomes according to the present invention, the liposomes preferably include one or more selected from compounds, microorganisms, proteins and enzymes. In this case, the compound is for example a pharmaceutical active ingredient or a functional health ingredient.

Meanwhile, a second embodiment of the present invention is directed to a method of preparing a liposome frozen powder which includes putting a container including liposomes in a container filled with one or more selected from isopropyl alcohol, ethanol and methanol, followed by lyophilization.

The method of preparing a liposome frozen powder according to the present invention is characterized in that liposomes are added to the container filled with one or more selected from isopropyl alcohol, ethanol and methanol, followed by lyophilization. When the container including liposomes is put in the container filled with the solvent, the time taken to cross the zone of maximum ice crystal formation is shortened, which can prevent deterioration in stability of liposome particles such as destruction of liposome structure and leakage of the active ingredient in the process of lyophilization. In addition, when the liposome frozen powder which has been lyophilized is dissolved again in an aqueous solution, upon use, it can be returned to the almost original state.

Meanwhile, with respect to the method of preparing a liposome frozen powder according to the present invention, the liposomes may be prepared by adding a cryoprotectant. The cryoprotectant preferably includes one or more selected from trehalose and sucrose.

In addition, with respect to the method of preparing a liposome frozen powder according to the present invention, the liposomes may be prepared by a method well-known in the art and are for example prepared by the process that includes mixing an organic solvent in which phospholipid is dissolved with distilled water in which trehalose is dissolved to produce inverted micelles (a), and mixing a solution containing the inverted micelles with distilled water in which sucrose is dissolved to prepare a double emulsion (b).

Meanwhile, with respect to the method of preparing a liposome frozen powder according to the present invention, the liposomes preferably include one or more selected from compounds, microorganisms, proteins and enzymes. In this case, the compound is for example a pharmaceutical active ingredient or a health functional ingredient.

Hereinafter, the present invention will be described in more detail with reference to the following Example and Test Example. The scope of the present invention is not limited to the following Example and includes modifications of the technical concept equivalent thereto.

MODE FOR INVENTION

Example 1: Production of Liposomes of the Present Invention 1 g of lecithin (from soybeans, llnshin wells) and 0.125 g of cholesterol (95%, Acros) were dissolved in 200 mL of a mixed solvent (ethyl acetate:n-hexane (4:1)) while stirring for 5 minutes. Then, 100 mL of water was added to the solution and sonication was conducted for one minute to form a W/0 emulsion. Then, a microfluidizer, which had been previously filled with the mixed solvent and had been maintained at 25° C. using a water circulator, was operated at a pressure of 1,000 bar to produce inverted micelles with a uniform size (preparation of homogeneous W/O emulsion).

Then, the inverted micelle-containing solution (W/O emulsion) and 600 mL of water were subjected to sonication for one minute to prepare a W/O/W emulsion. Then, a microfluidizer, which had been previously filled with water and had been maintained at 25° C. using a water circulator, was operated at a pressure of 500 bar to produce a double emulsion (containing liposomes) with a uniform size (preparation of homogeneous W/O/W emulsion).

Then, the double emulsion was stirred for 24 hours and the mixed solvent between lipid bilayers in the double emulsion was evaporated to prepare liposomes. After evaporation, the liposomes were stored under vacuum at 4° C.

Test Example 1: Selection of Organic Solvent in the Process of Producing Inverted Micelles Solvents which have similar features to chloroform conventionally used for the preparation of liposomes were selected from solvents registered in the Food Additive Code, and the selection was based on whether or not inverted micelles were formed well and were stably maintained without layer separation, when the solvents were used in the inverted micelle production, which was the first step of the double emulsion method. In addition, whether or not the W/O/W emulsion could be formed well when the produced inverted micelles were sonicated in distilled water was checked.

FIG. 1 shows results showing comparison in chemical properties between solvents registered in the Food Additive Code, and chloroform.

Inverted micelles were prepared using n-hexane, acetone, isopropyl alcohol, and ethyl acetate as solvents registered in the Food Additive Code as follows.

1 g of lecithin and 0.125 g of cholesterol were dissolved in 200 mL of a mixed solvent while stirring for 5 minutes. Then, 100 mL of water was added to the solution and sonication was conducted for one minute to form a W/0 emulsion. Then, a microfluidizer, which had been previously filled with an organic solvent and had been maintained at 25° C. using a water circulator, was operated at a pressure of 1,000 bar to produce inverted micelles with a uniform size (preparation of homogeneous W/O emulsion).

At this time, as shown in FIG. 2, n-hexane and ethyl acetate were layer-separated, immediately after the inverted micelles were produced, and a part of the inverted micelles was destroyed over time. In addition, for the inverted micelles, based on the phospholipid boundary, water should be present in the central part and the organic solvent should be in the periphery. In the case of isopropyl alcohol and acetone, as shown in FIG. 2, 100% of the organic solvent was dissolved in water so that phospholipid could not create inverted micelles well and was dispersed. For this reason, layer separation did not occur, but in the second step, the W/O/W emulsion step, a lipid bilayer could not be formed and micelles were scattered.

FIG. 2 shows inverted micelles produced using, as a solvent, n-hexane, ethyl acetate, acetone and isopropyl alcohol.

Meanwhile, a mixed solvent advantageous in forming inverted micelles was prepared based on the features of solvents shown in FIG. 1. For this purpose, the solvent should not be dissolved in water and should have similar viscosity and polarity to chloroform. Inverted micelles were produced by mixing ethyl acetate, which has the most similar properties to chloroform under these conditions, with n-hexane, acetone or isopropyl alcohol in respective predetermined volume ratios. In particular, in the case of mixing ethyl acetate with n-hexane, layer separation was the least.

Meanwhile, in the case of ethyl acetate and n-hexane, there were considered to be problems associated with polarity and viscosity which are required to form inverted micelles. Accordingly, attempts were made to improve the chemical properties of the solvents by changing a mix ratio between the two solvents.

Whether or not layer separation occurred when the inverted micelles were produced using ethyl acetate and n-hexane in a mix ratio of 1:1, 2:1, 3:1, 4:1 or 5:1 and were then allowed to stand at room temperature was checked.

As a result, it was confirmed that the shapes of inverted micelles were maintained well in the mix ratio of ethyl acetate to n-hexane of 3:1 to 5:1 (v/v) among various mix ratios of the mixed solvents. When the mix ratio of ethyl acetate to n-hexane was 4:1 (v/v), the shapes of inverted micelles were confirmed to be maintained the most, as shown in FIG. 3.

FIG. 3 shows inverted micelles produced using a mixed solvent of ethyl acetate and n-hexane at different mix ratios of 1:1, 2:1, 3:1, 4:1, and 5:1.

Test Example 2: Analysis of Liposomes Produced Using Mixed Solvent of Ethyl Acetate and n-Hexane After inverted micelles were produced using a mixed organic solvent of ethyl acetate and n-hexane in a mix ratio of 4:1 in Test Example 1, double emulsions were sequentially prepared and then the organic solvents were evaporated to produce liposomes. Then, liposomes were subjected to dynamic light scattering (DLS), transmission electron microscopy (TEM) and Laurdan analysis.

(1) Dynamic Light Scattering (DLS)

Size distribution and uniformity of liposomes were measured using a zeta potential analyzer (Zetasizer nano ZS, Malvern instruments Ltd, 1XZ, UK). 1.0 mL of a liposome solution was charged in a disposable plastic cuvette and measurement was repeated three times. Measurement conditions were refractive index (1.330), viscosity (0.8872 cP), equilibration time (1 min), measurement temperature (25° C.) and measurement angle (173° backscattering).

Analysis results showed that, as shown in FIG. 4A, regarding the particle distribution of the liposome solution, size and uniformity were confirmed as a mean size of 98.68 nm and PdI (polydiversity index) of 0.177.

(2) Transmission Electron Microscopy (TEM)

For morphological analysis, uranyl acetate was used as a negative staining reagent of liposomes. The overall process was as follows. 10 μL of a liposome solution was loaded on a Formvar-coated silicon monoxide grid (200 mesh). After one minute, a 2% uranyl acetate solution was placed on the grid. After one minute, the grid was washed with distilled water. After the grid was dried at room temperature, the liposomes were observed by TEM (120 keV, JEOL Ltd., Tokyo, Japan).

Analysis results showed that, as shown in FIG. 4B, liposomes took the form of a sphere and showed uniformity, without morphological aggregation and destruction.

(3) Laurdan Analysis

10 μL of a 10 mg/mL Laurdan solution was added to 10 mL of a liposome solution (final molar ratio 1000:1). Then, the mixture was incubated at room temperature for 30 minutes and then fluorescence was measured. Fluorescence of the solution (mixture) was measured under Laurdan emission spectra ranging from 380 nm to 550 nm and a constant excitation wavelength of 340 nm using a fluorescence spectrophotometer (SpectraMax i3, Molecular Devices, Austria). At this time, GP (generalized polarization) was calculated from emission spectra in accordance with the following Equation 1:

[Equation 1]

wherein $I_{440}$ and $I_{490}$ mean fluorescence emission intensity at 440 and 490 nm, respectively.

In addition, GP is an indicator showing flowability of liposome bilayers and is a method that uses the feature that peak shift occurs from 440 nm to 490 nm depending on change of bilayers when Laurdan, as a fluorescence probe is inserted into the liposome bilayers. When the intact liposome bilayer is maintained in consideration of properties of liposomes (lipid composition and cholesterol proportion) of the present invention, its flowability corresponds to GP=0.5, and when the liposome bilayer is destroyed or deformed, its flowability is decreased to GP=0.3 to −0.3.

Analysis results showed that GP was 0.49, which means that the liposome bilayer structure and bilayer flowability were the same as when chloroform is conventionally used as a solvent for dissolving phospholipids.

FIG. 4A is a size distribution (DLS) graph of liposomes produced using a mixed solvent of ethyl acetate and n-hexane in a ratio of 4:1 and FIG. 4B is a TEM image of the liposomes.

Example 2: Production of Liposome Frozen Powder of the Present Invention 1 g of lecithin (from soybeans, Ilshin wells) and 0.125 g of cholesterol (95%, Acros) were dissolved in 200 mL of chloroform (Samchun) while stirring for 5 minutes. The phospholipid solution, and a solution obtained by dissolving 0.001 g of calcein (Sigma), 5 g of trehalose (cryoprotectant, (D(+)-trehalose dihydrate, 99% (Acros)) in 100 mL of water while stirring for 5 minutes were sonicated for one minute to prepare a W/0 emulsion.

Then, a microfluidizer, which had been previously filled with chloroform and had been maintained at 25° C. using a water circulator, was operated for 10 cycles at a pressure of 1,000 bar to produce inverted micelles with a uniform size (preparation of homogeneous W/O emulsion).

Then, 5 g of sucrose (Sigma) was dissolved in 600 mL of water while stirring for 5 minutes, and the resulting solution and the inverted micelle-containing solution (W/O emulsion) were subjected to sonication for one minute to prepare a W/O/W emulsion. Then, a microfluidizer, which had been previously filled with water and had been maintained at 25° C. using a water circulator, was operated for 5 cycles at a pressure of 500 bar to prepare a double emulsion (containing liposomes) with a uniform size (preparation of homogeneous W/O/W emulsion).

Then, the double emulsion was stirred for 24 hours and the organic solvent between lipid bilayers in the double emulsion was evaporated to prepare liposomes. After evaporation, the liposomes were stored under vacuum at 4° C.

The produced liposomes were lyophilized as follows.

The liposome solution was fractioned in an amount of 10 mL in 50 mL conical tubes and each conical tube was placed in a container including liquid (IPA) such that the liposome solution was immersed. Then, the conical tube was frozen in a deep freezer at −80° C. for 8 hours. Then, the frozen liposome solution was lyophilized at −80° C. for 48 hours. After lyophilization, the powder was stored under vacuum at 4° C.

Figure 5:
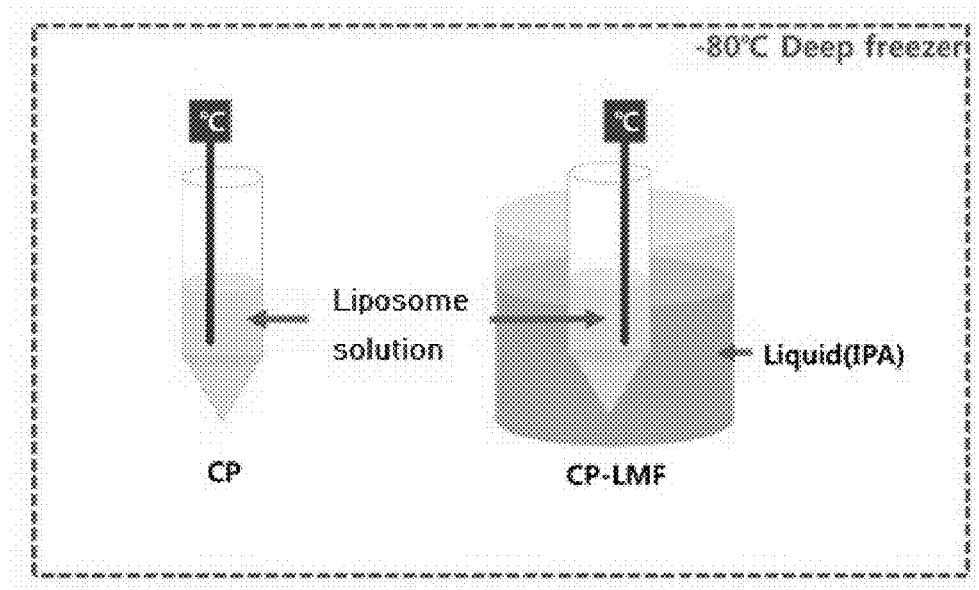
FIG. 5 is a schematic diagram showing "CP (cryoprotectant)" and "CP-LMF (cryoprotectant-liquid mediated freezing)"

At this time, the case where the conical tube including the liposome solution was placed in the container including liquid (IPA) or the resulting liposome frozen powder was referred to as "CP-LMF (cryoprotectant-liquid mediated freezing)" and the case where this process was not conducted or the resulting liposome frozen powder was referred to as "CP (cryoprotectant)" (see FIG. 5).

FIG. 5 is a schematic diagram showing "CP (cryoprotectant)" and "CP-LMF (cryoprotectant-liquid mediated freezing)".

Meanwhile, a freezing curve was measured to check whether or not the time taken to pass the zone of maximum ice crystal formation could be shortened by putting the conical tube including the liposome solution in the container including liquid (IPA). Measurement was conducted as follows.

In the process of freezing during lyophilization, change in temperature of the liposome solution was measured. The liposome solution was fractioned in an amount of 10 mL in 50 mL conical tubes, and a thermometer was put in the solution. "CP" was frozen while the conical tube was exposed to the air, while "CP-LMF" was frozen while the conical tube was immersed in a liquid (IPA). The temperature of the solution was measured each minute over 60 minutes.

Figure 6:
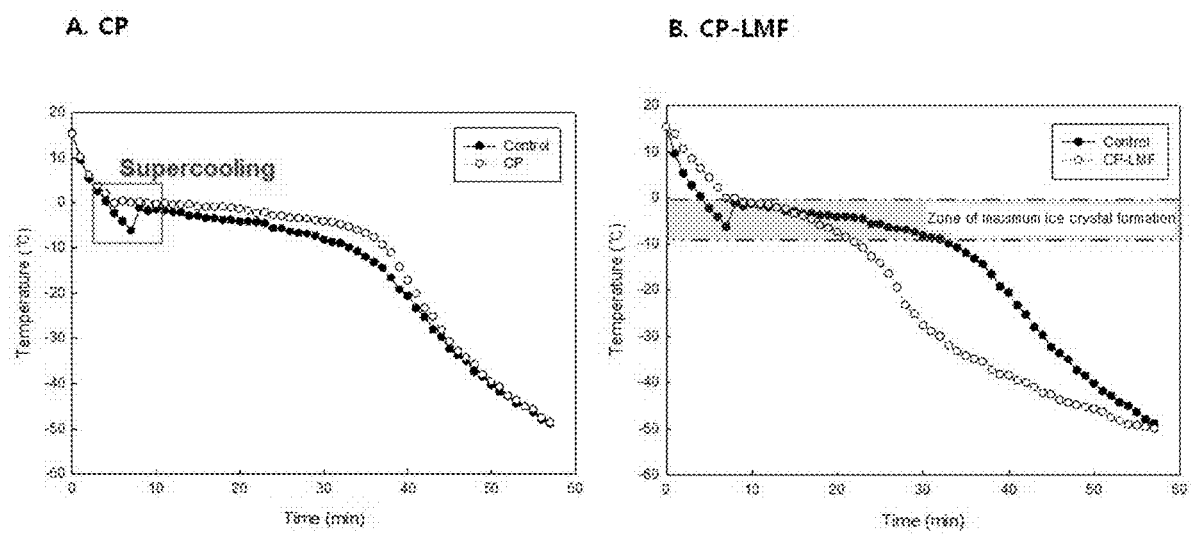
FIG. 6A is a graph showing a temperature change behavior by "CP (cryoprotectant)" and FIG. 6B is a graph showing a temperature change behavior by "CP-LMF (cryoprotectant-liquid mediated freezing)"

Measurement results showed that, as can be seen from FIG. 6, "CP" using only the cryoprotectant inhibited supercooling, while "CP-LMF" inhibited supercooling and halved the time taken to pass the zone of maximum ice crystal formation (0 to −10° C.)

FIG. 6A is a graph showing a temperature change behavior by "CP (cryoprotectant)" and FIG. 6B is a graph showing a temperature change behavior by "CP-LMF (cryoprotectant-liquid mediated freezing)".

Test Example 3: Analysis of Liposome Frozen Powder

After the lyophilization in Example 2, the state of the liposome powder was checked, and the liposome powder was subjected to redispersion, dynamic light scattering (DLS), transmission electron microscopy (TEM), and Laurdan analysis.

(1) Powder State and Redispersion

Whether or not the liposome structure after lyophilization could be maintained well, as compared to the original state, was checked, as the time taken to pass the zone of maximum ice crystal formation was controlled. First, the state of powder and whether or not the powder was dispersed well when rehydrated were checked.

"CP-LMF" took the form of a non-agglomerated fine powder and had an impregnation proportion of 39.7% when rehydrated, which means that 85% or more of the central ingredient was maintained, compared to 46.5% before lyophilization. On the other hand, "CP" not using LMF (liquid mediated freezing) showed powder agglomeration as well as powder discoloration which results from leakage of most of the central ingredient.

Figure 7:
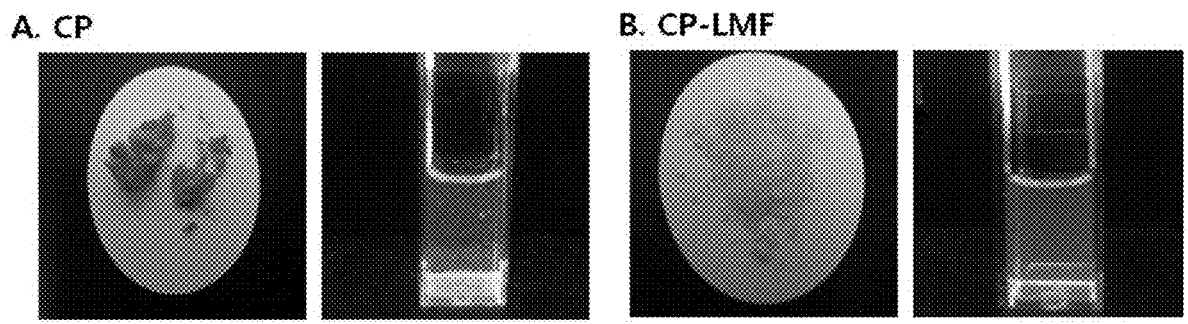
FIG. 7A is an image showing a "CP (cryoprotectant)" powder and a liposome solution upon rehydration.
FIG. 7B is an image showing a "CP-LMF (Cryoprotectant-Liquid mediated freezing)" powder and a liposome solution upon rehydration.

In addition, regarding dispersibility, "CP-LMF" was dispersed immediately after rehydrated, but "CP" was not dispersed well after rehydrated (FIGS. 7A and 7B).

FIG. 7A is an image showing a "CP (cryoprotectant)" powder and a liposome solution upon rehydration, and FIG. 7B is an image showing a "CP-LMF (cryoprotectant-liquid mediated freezing)" powder and a liposome solution upon rehydration.

(2) Dynamic Light Scattering (DLS)

DLS analysis was conducted in the same manner as in Test Example 2.

Analysis results showed that, compared to the particle distribution (mean size=135 nm, PdI (polydiversity index)=0.074) of the liposome solution before lyophilization, "CP-LMF" maintained similar size and uniformity (i.e., mean size=164 nm, PdI=0.120), while "CP" did not maintain the size and uniformity (i.e., mean size=361 nm, PdI=0.268) (FIGS. 8A, 8B and 8C, and FIG. 9).

Figure 8:
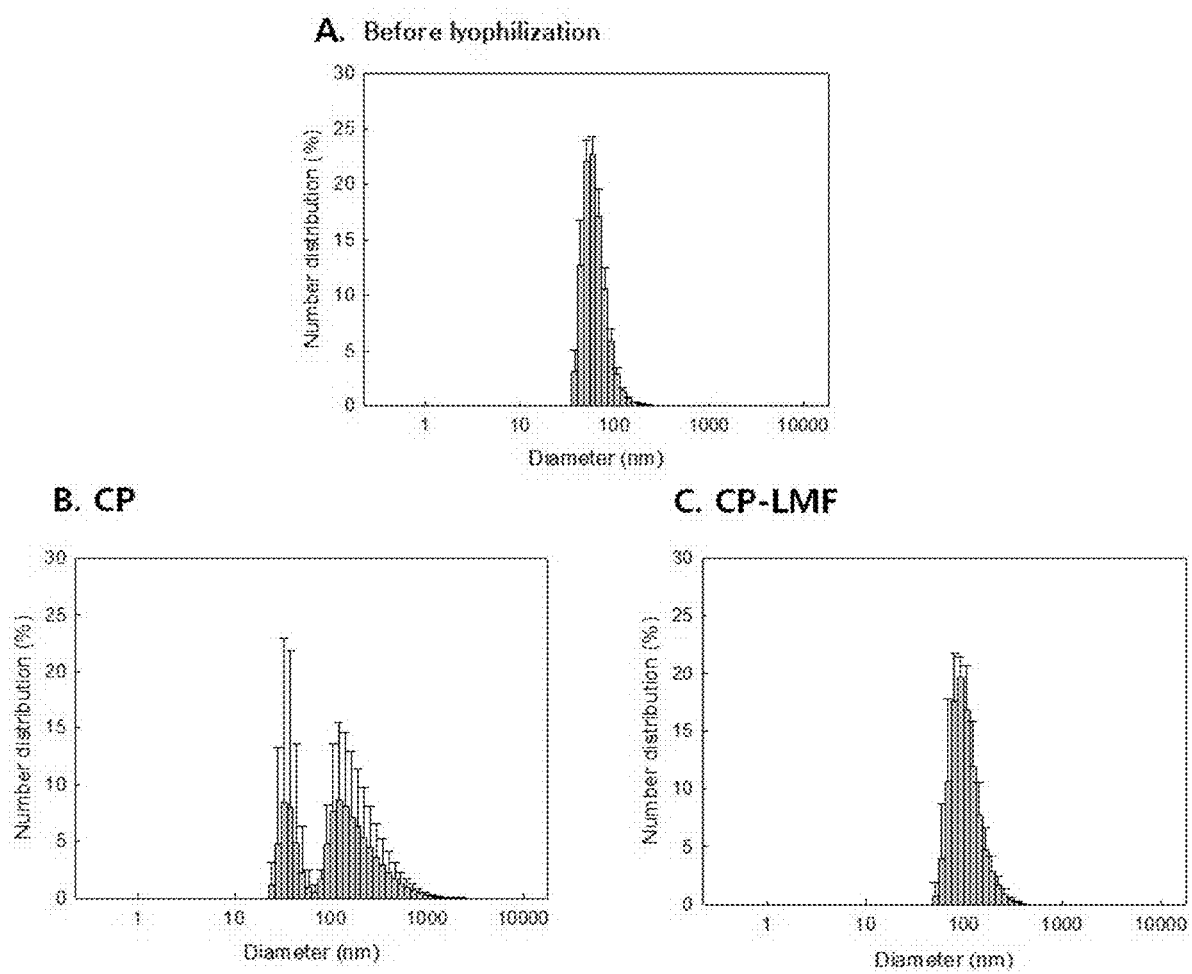
FIG. 8A is a DLS particle distribution graph of the liposome solution before lyophilization.
FIG. 8B is a DLS particle distribution graph of the "CP" liposome solution and FIG. 8C is a DLS particle distribution graph of the "CP-LMF" liposome solution.

FIG. 8A is a DLS particle distribution graph of the liposome solution before lyophilization, FIG. 8B is a DLS particle distribution graph of the "CP" liposome solution and FIG. 8C is a DLS particle distribution graph of the "CP-LMF" liposome solution.

Figure 9:
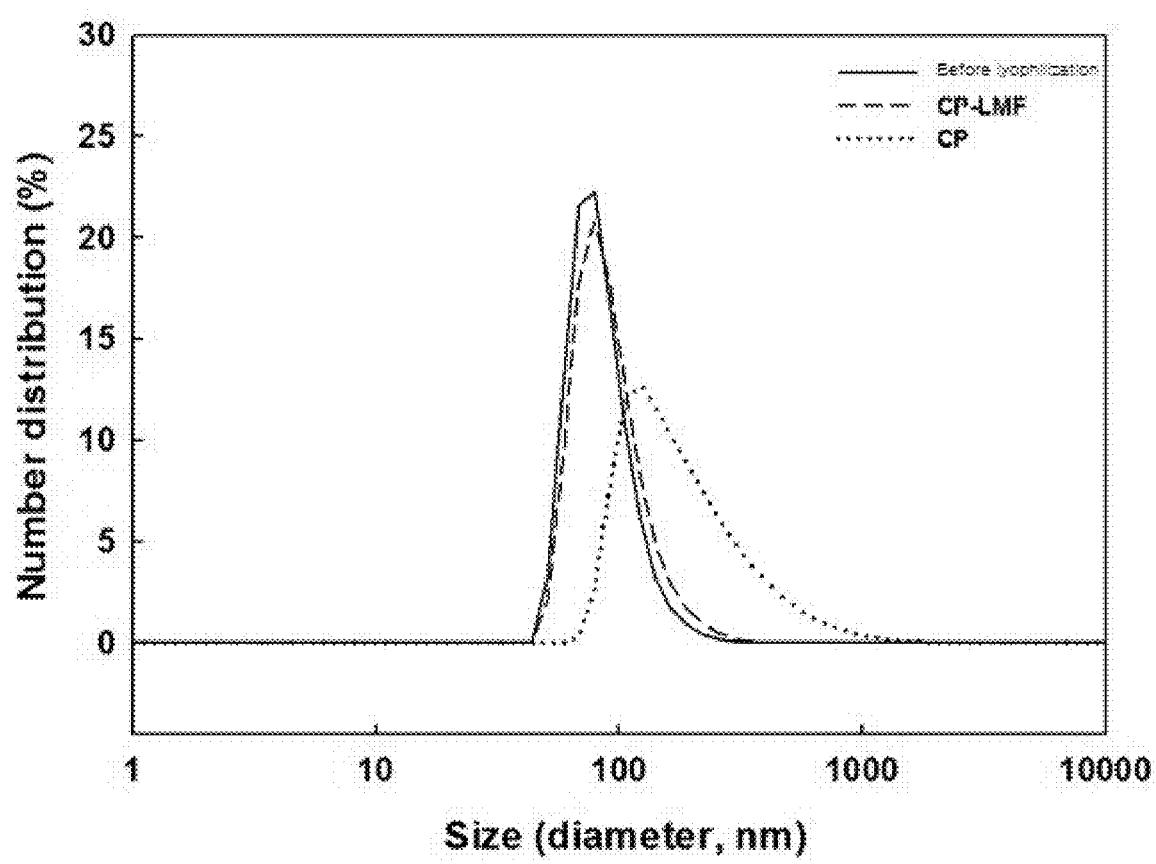
FIG. 9 is a graph showing comparison in DLS particle distribution between the liposome solution before lyophilization, and "CP" and "CP-LMF" liposome solutions.

FIG. 9 is a graph showing comparison in DLS particle distribution between the liposome solution before lyophilization, and "CP" and "CP-LMF" liposome solutions.

(3) Transmission Electron Microscopy (TEM)

TEM analysis was conducted in the same manner as in Test Example 2.

Analysis results showed that "CP-LMF" maintained a similar spherical shape to the liposome before lyophilization and kept a mean size of 100 nm and its bilayer structure. On the other hand, "CP" showed a destroyed and agglomerated liposome structure (FIGS. 10A, 10B and 10C).

Figure 10:
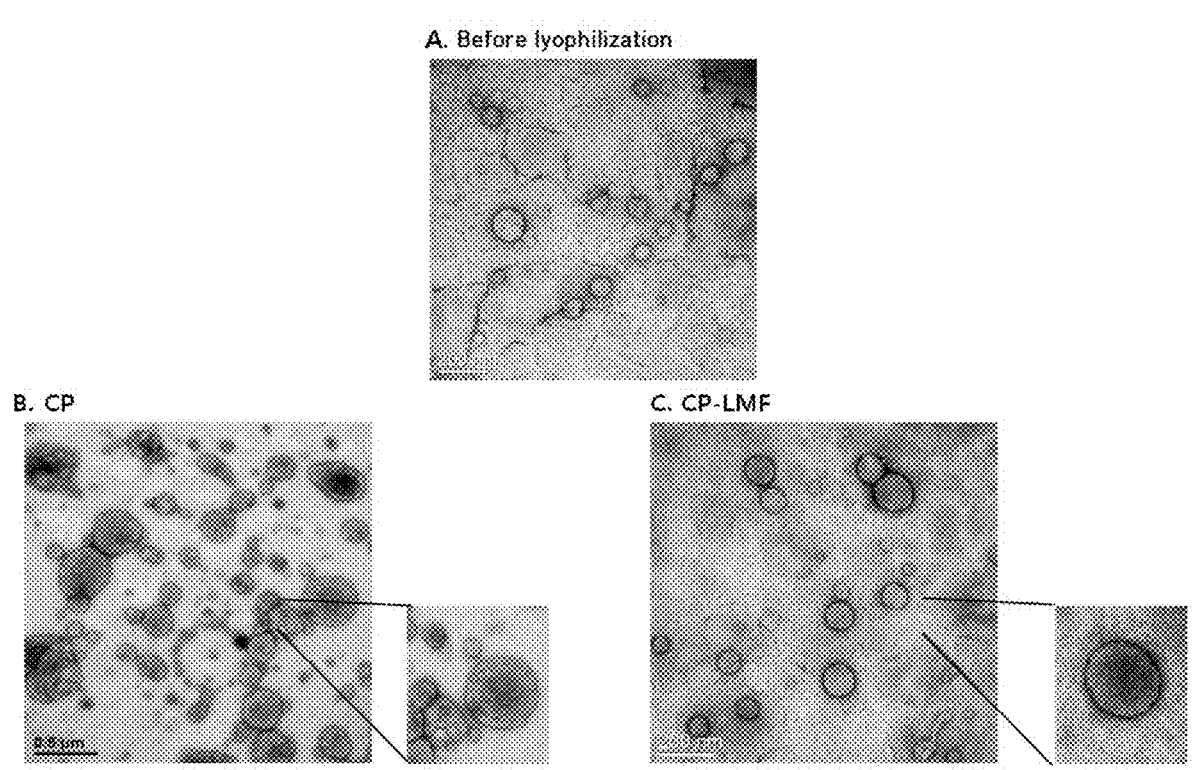
FIG. 10A is a TEM image of the liposome solution before lyophilization.
FIG. 10B is a TEM image of the "CP" liposome solution.
FIG. 10C is a TEM image of the "CP-LMF" liposome solution.

FIG. 10A is a TEM image of the liposome solution before lyophilization, FIG. 10B is a TEM image of the "CP" liposome solution, and FIG. 10C is a TEM image of the "CP-LMF" liposome solution.

(4) Laurdan Analysis

Laurdan analysis was conducted in the same manner as in Test Example 2.

Analysis results showed that the liposome solution before lyophilization had a GP of 0.50, CP-LMF had a GP of 0.50 which was the same as before lyophilization, and CP had a decreased GP of 0.36.

Figure 11:
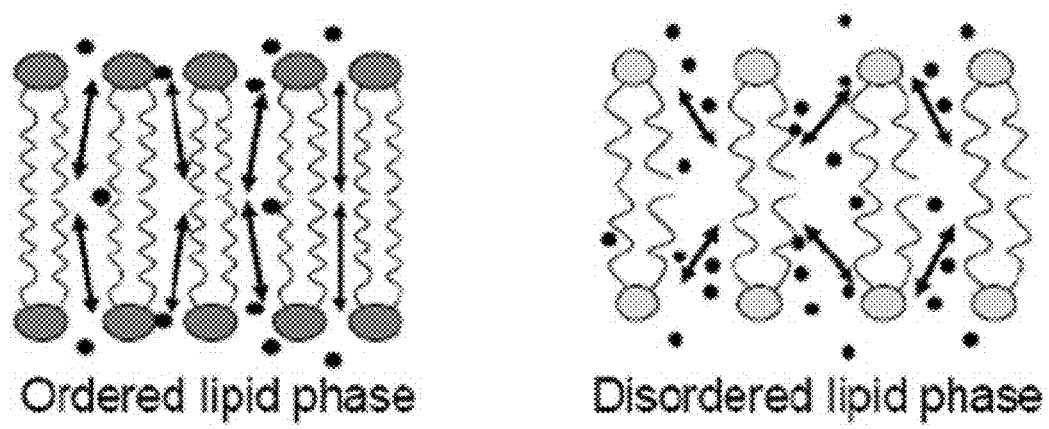
FIG. 11 is a schematic diagram showing an ordered lipid phase and a disordered lipid phase.

The reason for decrease in GP may be considered that, inner and outer parts of liposomes volumetrically expand due to growth of ice crystals, which causes liposome bilayer structures to be changed and thus destroyed or disordered (see FIG. 11).

FIG. 11 is a schematic diagram showing an ordered lipid phase and a disordered lipid phase.

Test Example 4: Identification of Availability of Solvents Other than Isopropyl Alcohol Whether or not solvents excluding isopropyl alcohol have the same functions on LMF (liquid mediated freezing) lyophilization was identified.

Using alcohol (methanol, ethanol, 1-propanol, 1-butyl alcohol) solvents and acetone that have similar molecular structure and melting point to isopropyl alcohol, instead of isopropyl alcohol, liposomes were lyophilized in the same manner as in Example 2 and then rehydrated, and particle distribution thereof was confirmed by DLS.

As a result, when methanol and ethanol were used, particle distributions were similar to when isopropyl alcohol was used, and when 1-propanol and 1-butyl alcohol were used, particle distribution was uniform, but the particle size was increased to 40 nm or more, compared to the counterpart size. In addition, acetone showed the same distribution as when LMF lyophilization was not conducted.

Figure 12:
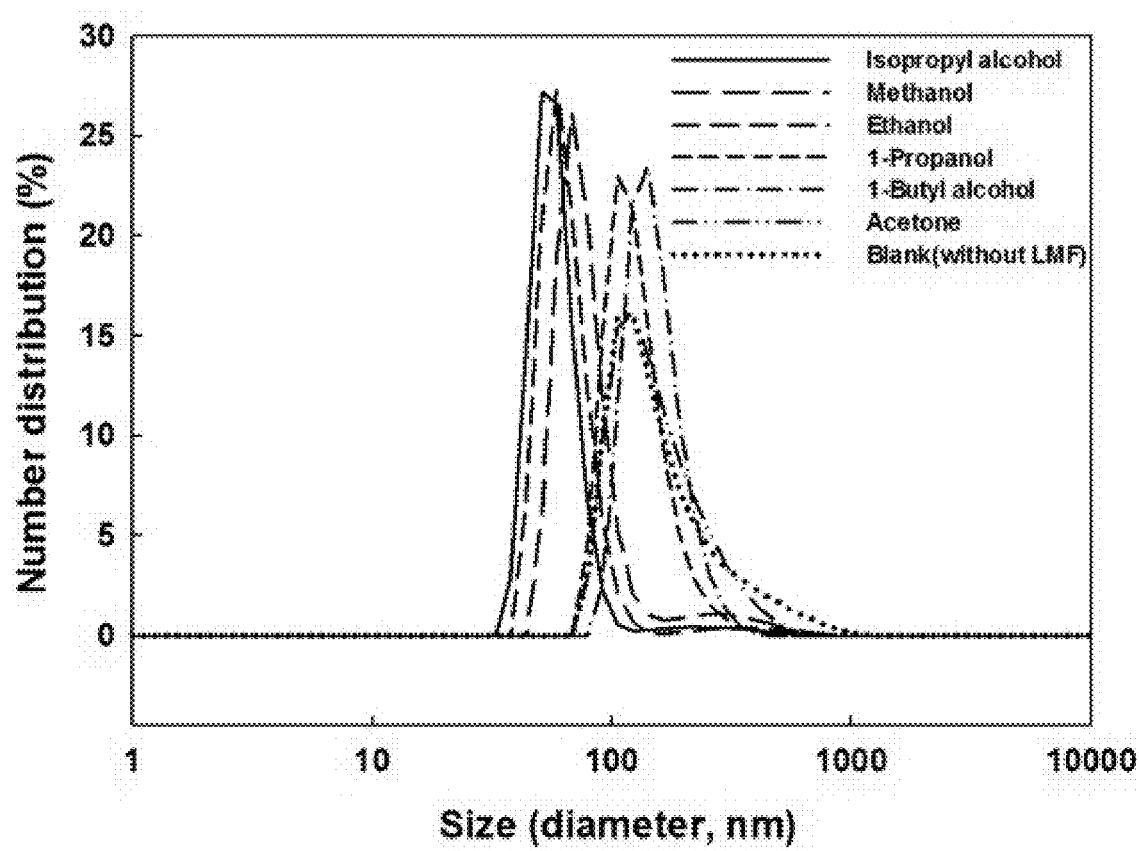
FIG. 12 is a particle distribution graph of liposome solutions after lyophilization and rehydration depending on the type of solvent based on LMF (liquid mediated freezing)

These results indicated that methanol and ethanol could also exert the same constant-rate elevated-temperature effects and thus same lyophilization effects as isopropyl alcohol (FIG. 12).

FIG. 12 is a particle distribution graph of liposome solutions after lyophilization and rehydration depending on the type of solvent based on LMF (liquid mediated freezing).

Example 3: Production of Liposome Including Marker

The present invention aims to select solvents optimal for the production of liposomes from solvents that can be used in food, determine optimal mixing conditions thereof and improve conventional lyophilization methods to complete powderization and thereby enable redispersion at room temperature without an additional process.

In the present invention, a marker was used to identify whether or not liposomes could maintain their shapes and could effectively maintain their impregnation proportion, even after powderization as a drug carrier.

The marker used in the present invention was a branched amino acid (BCAA) which has potent anticancer and anti-inflammatory activities. However, the marker has a drawback of low bioavailability. Nevertheless, it was chosen because bioavailability is considered to be improved through impregnation in the liposome.

The liposome production method used in the present invention was a W/O/W emulsion method and the overall process thereof is as follows.

First, 100 mL of distilled water in which 2% BCAA and 5% trehalose (cryoprotectant) were dissolved was thoroughly mixed with 200 mL of a mixed solvent (ethyl acetate:n-hexane(4:1)) in which 2.5% lecithin was dissolved at 12,000 rpm using Ultra-Turrax for 5 minutes and inverted micelles with a uniform size were then produced using a microfluidizer for 10 cycles at a pressure of 15,000 psi.

Then, 300 mL of an inverted micelle-containing solution and 600 mL of distilled water, in which 5% sucrose (cryoprotectant) was dissolved, were mixed at 12,000 rpm for minutes and 900 mL of a double emulsion (containing liposomes) with a uniform size was prepared using a microfluidizer for 5 cycles at a pressure of 5,000 psi.

Then, the double emulsion solution was fractioned in an amount of 10 mL in conical tubes. Then, each conical tube was charged in a container filled with isopropyl alcohol and stored in a deep freezer at −80° C. overnight. Then, the conical tube was lyophilized in a freeze-dryer at −80° C. for 48 hours.

Figure 13:
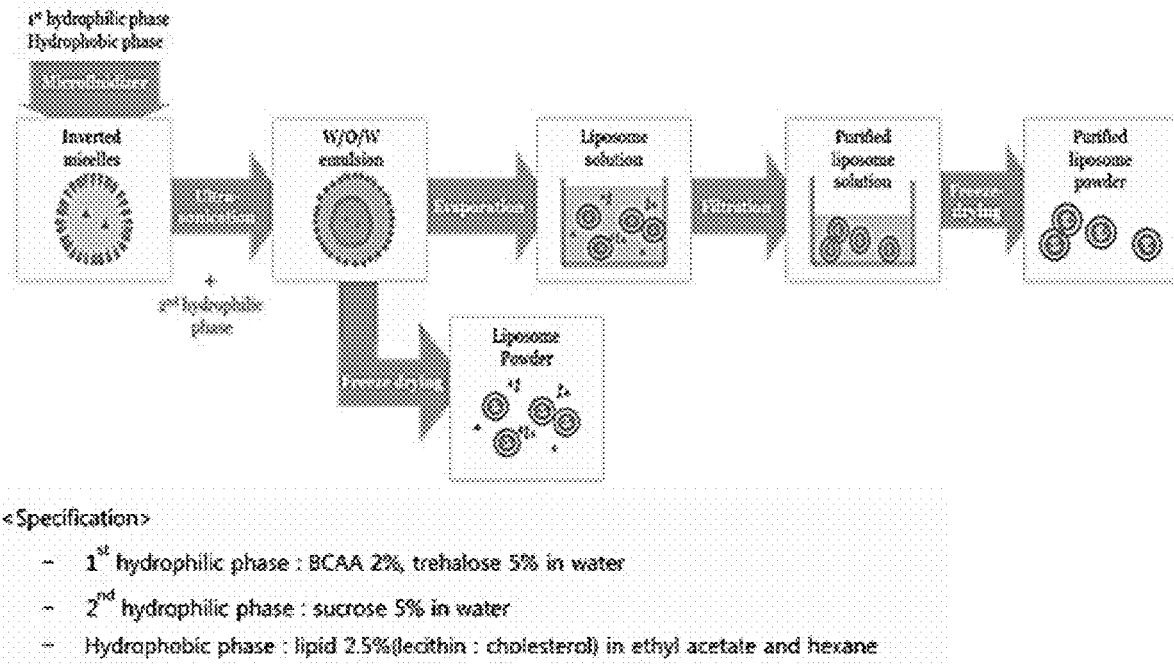
FIG. 13 is a schematic diagram illustrating the overall process of producing marker-including liposomes.

FIG. 13 is a schematic diagram illustrating the overall process of producing marker-including liposomes.

Test Example 5: Selection of Organic Solvent During Production of Inverted Micelles in the Process of Producing Marker-Including Liposomes Solvents which have similar features to chloroform conventionally used for the preparation of liposomes were selected from the solvents registered in the Food Additive Code, and the selection was based on whether or not inverted micelles were formed well and were stably maintained without layer separation, when the solvents were used in the production of inverted micelles, which was the first step of the double emulsion method. In addition, whether or not the W/O/W emulsion could be formed well when the prepared inverted micelles were sonicated in distilled water was checked.

Inverted micelles were produced using n-hexane, acetone, isopropyl alcohol and ethyl acetate as solvents registered in the Food Additive Code as follows.

Figure 14:
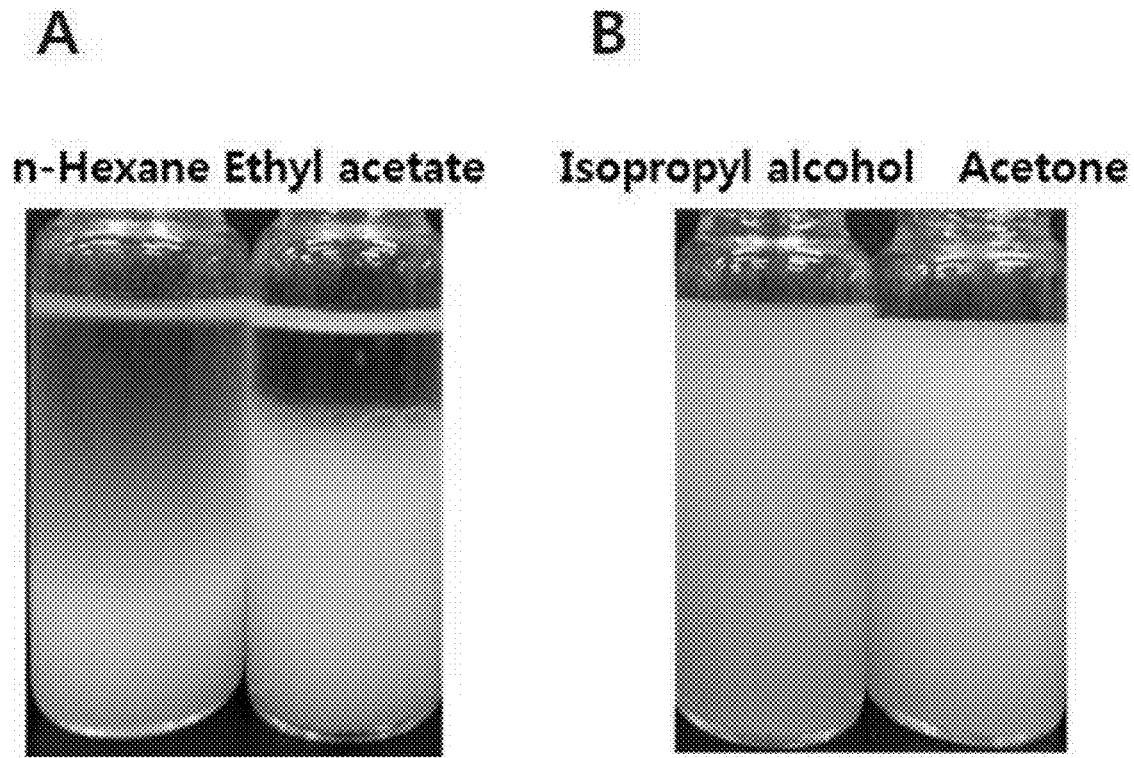
FIG. 14A shows inverted micelles produced using n-hexane and ethyl acetate.
FIG. 14B shows inverted micelles produced using isopropyl alcohol and acetone.

5 mL of distilled water was added to 10 mL of an organic solvent, in which 2.5% lecithin was dissolved, and the solution was sonicated using Ultra-Turrax at 12,000 rpm for 5 minutes and allowed to stand at room temperature. At this time, whether or not layer separation occurred was checked. In the case of n-hexane and ethyl acetate, layer separation occurred, as shown in FIG. 14A. In addition, in the case of isopropyl alcohol and acetone, as shown in FIG. 14B, layer separation did not occur, but because solubility in water was 100%, a W/O/W emulsion could not be formed when the produced inverted micelles were added to distilled water.

FIG. 14A shows inverted micelles produced using n-hexane and ethyl acetate, and FIG. 14B shows inverted micelles produced using isopropyl alcohol and acetone.

Meanwhile, in the case of ethyl acetate and n-hexane, there were considered to be problems associated with polarity and viscosity which are required to form inverted micelles. Accordingly, attempts were made to improve the chemical properties of the solvents by changing a mix ratio between the two solvents.

Whether or not layer separation occurred was checked when ethyl acetate and n-hexane were mixed in a ratio of 5:1, 4:1, 3:1, 2:1, 1:1, 1:2, 1:3, 1:4 or 1:5, lecithin was dissolved at 2.5% in 10 mL of the mixed solvent, 5 mL of distilled water was added thereto, sonication was conducted for 5 minutes using Ultra-Turrax at 12,000 rpm and then the resulting reaction was stored at room temperature. At this time, whether or not layer separation occurred was checked.

As a result, it was confirmed that the shapes of inverted micelles were maintained well in the mix ratio of ethyl acetate to n-hexane of 3:1 to 5:1 (v/v), among various mix ratios of the mixed solvents. When the mix ratio of ethyl acetate to n-hexane was 4:1 (v/v), the shapes of inverted micelles were confirmed to be maintained the most, as shown in FIG. 15.

Figure 15:
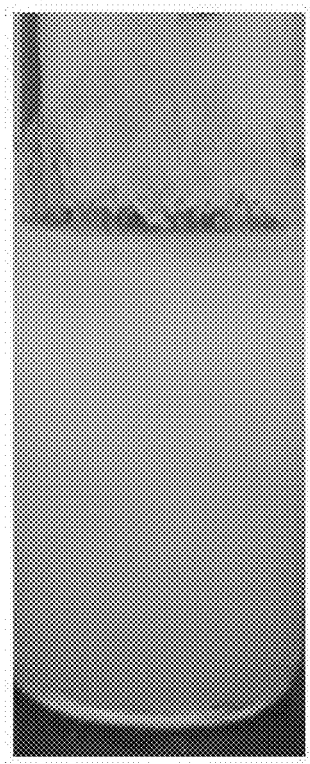
FIG. 15 shows inverted micelles produced using a mixed solvent of ethyl acetate and n-hexane in a mix ratio of 4:1.

FIG. 15 shows inverted micelles produced using a mixed solvent of ethyl acetate and n-hexane in a mix ratio of 4:1.

Meanwhile, inverted micelles were produced using a mixed organic solvent of ethyl acetate and n-hexane in a mix ratio of 4:1, double emulsions were sequentially prepared and then the organic solvents were evaporated to produce marker-including liposomes.

Figure 16:
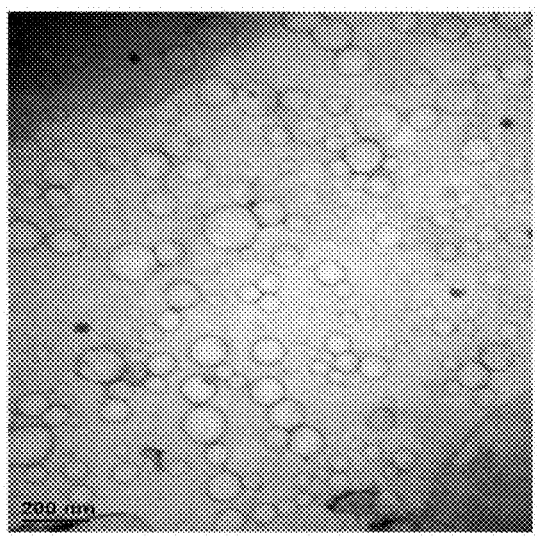
FIG. 16A is a TEM image of marker-including liposomes produced using a mixed solvent of ethyl acetate and n-hexane in a ratio of 4:1
FIG. 16B is a size distribution (DLS) graph of the liposomes.
Figure 16:
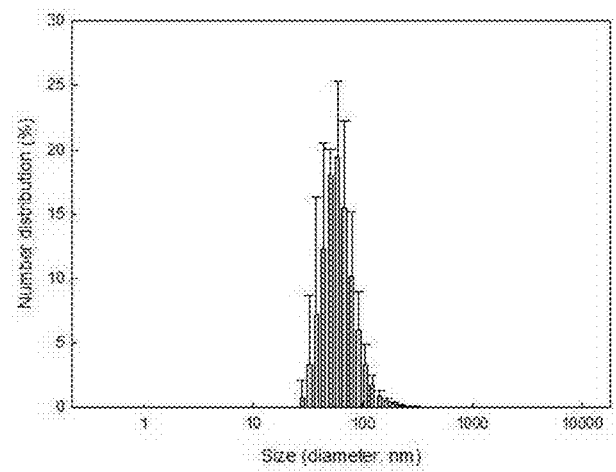

TEM analysis confirmed that, as shown in FIG. 16, about 100 nm liposomes were formed, and DLS analysis identified that the about 100 nm liposomes had a uniform size distribution of PdI=0.3 or less. At this time, the impregnation proportion of BCAA use as a marker was 20%, which demonstrates that BCAA was impregnated in the liposomes.

FIG. 16A is a TEM image of marker-including liposomes produced using a mixed solvent of ethyl acetate and n-hexane in a ratio of 4:1 and FIG. 16B is a size distribution (DLS) graph of the liposomes.

Test Example 6: Improvement in Lyophilization Process of Marker-Including Liposomes Liposomes were frozen in a deep freezer at −80° C. using trehalose and sucrose as cryoprotectants as disclosed in Reference dissertation related to conventional lyophilization and were then lyophilized using a freeze dryer for 48 hours.

Figure 17:
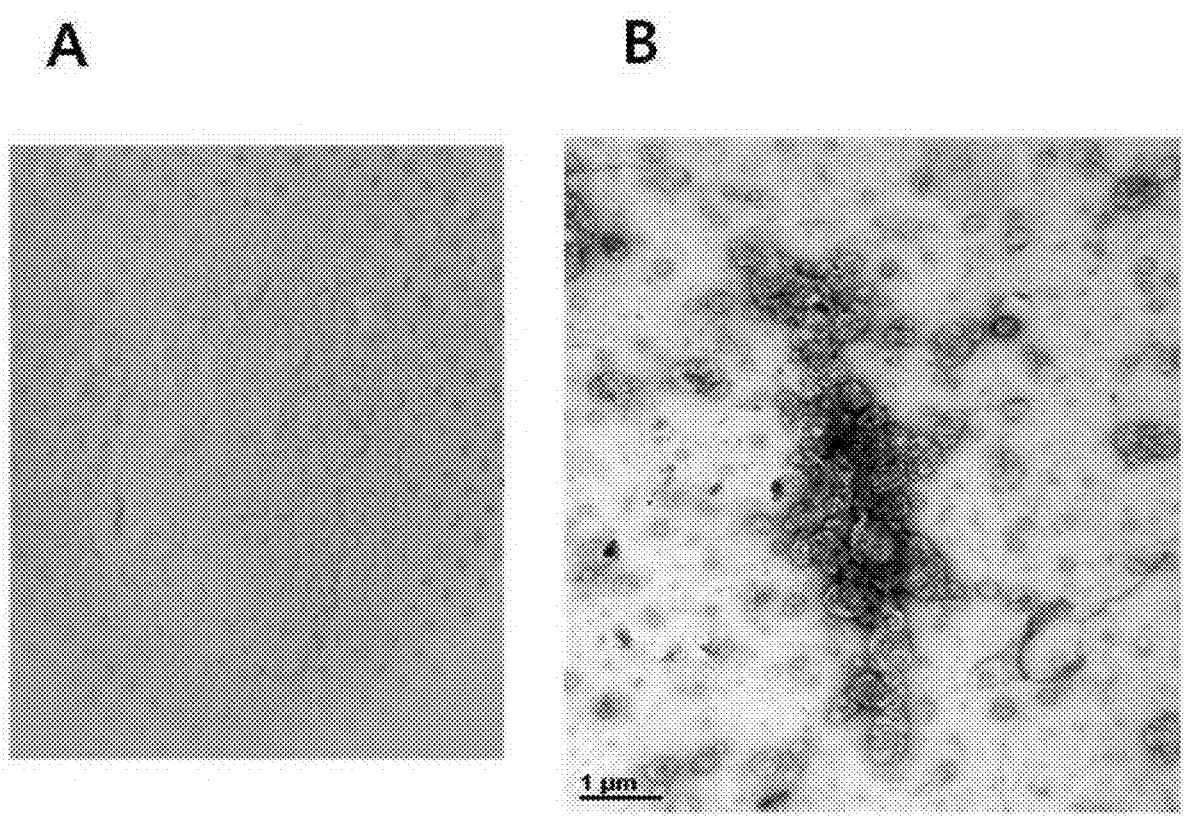
FIG. 17A shows marker-including liposomes produced in the form of a yellow powder after lyophilization and FIG. 17B is a TEM image of the marker-including liposomes.

As a result, a yellow powder was obtained as shown in FIG. 17A. However, the powder was rapidly oxidized at room temperature, and was not soluble well even after vortexing for 30 minutes or longer, when rehydrated in the same amount of distilled water as before lyophilization. When the powder was analyzed by TEM, the structure of liposomes was destroyed and the powder was agglomerated as shown in FIG. 17B. The reason for this was that the structure of liposomes was destroyed due to expansion of water molecule crystals in the liposomes upon rapid freezing.

FIG. 17A shows marker-including liposomes produced in the form of a yellow powder after lyophilization and FIG. 17B is a TEM image of the marker-including liposomes.

It was considered that, in an attempt to prevent destruction of the liposome structure during lyophilization, constant temperature drop and slow freezing were needed when cooled to −80° C. in a deep freezer. Accordingly, a method of cooling liposomes in an isopropyl alcohol container was introduced.

Figure 18:
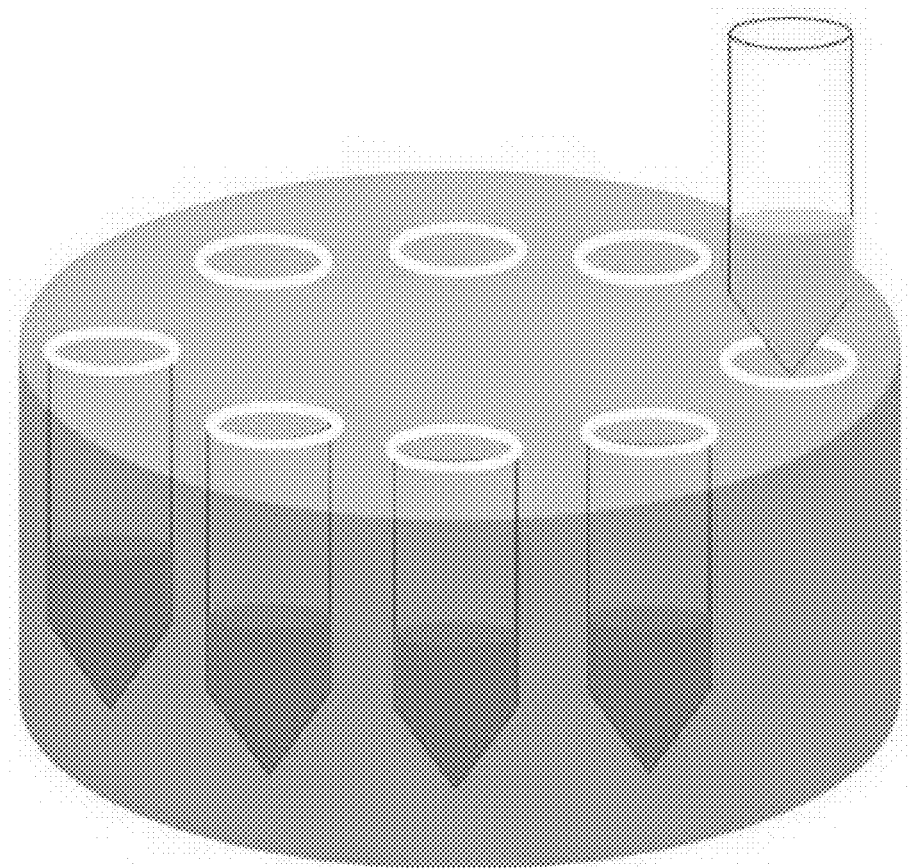
FIG. 18 is a schematic diagram illustrating an isopropyl alcohol container.

As shown in FIG. 18, when a conical tube including a liposome solution, which was immersed in an isopropyl alcohol container, was frozen, the liposomes were slowly frozen while the temperature of the solution was decreased at a constant rate of 1° C./min. Taking this point into consideration, the conical tube including 10 mL of the liposome solution, which was put in the isopropyl alcohol container, was stored at −80° C. in a deep freezer overnight and lyophilized at −80° C. for 48 hours.

FIG. 18 is a schematic diagram illustrating an isopropyl alcohol container.

Figure 19:
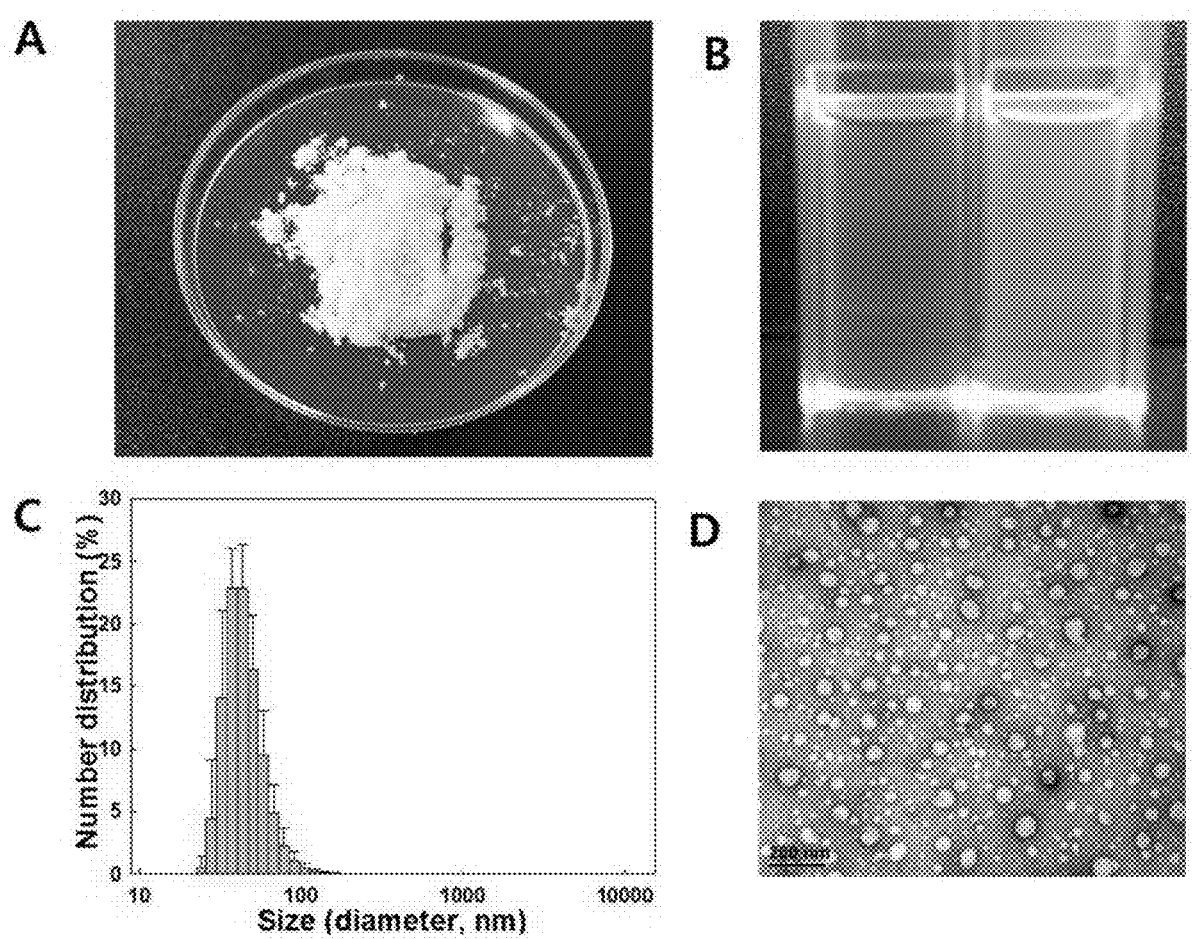
FIG. 19A shows a shape of marker-including liposome powder after lyophilization.
FIG. 19B shows a state in which the marker-including liposome powder is dissolved in distilled water.
FIG. 19C shows size distribution (DLS)
FIG. 19D shows results of morphological analysis (TEM) of the marker-including liposomes.

Test results showed that a white (no lecithin leakage) powder was obtained, as shown in FIG. 19, and the powder was rapidly dispersed without the necessity of additional heating or vortexing when rehydrated, and TEM and DLS analysis showed that uniform liposomes with a size of about 100 nm maintained their shapes. In addition, the impregnation proportion of BCAA used as a marker was maintained at 20%, which was the same as before lyophilization.

FIG. 19A shows a shape of marker-including liposome powder after lyophilization, FIG. 19B shows a state in which the marker-including liposome powder is dissolved in distilled water, FIG. 19C shows a size distribution (DLS) graph, and FIG. 19D shows results of morphological analysis (TEM) of the liposome.

Meanwhile, since the constant-rate elevated-temperature effect of the isopropyl alcohol container was considered to be due to the molecular structure or low melting point of −89° C., a container was prepared using three solvents of ethanol (−114° C.), methanol (−97.5° C.), and acetone (−95° C.), which have similar structure to isopropyl alcohol and a lower melting point, excluding isopropyl alcohol, and whether or not the container had similar effects to the isopropyl alcohol container was tested.

Figure 20:
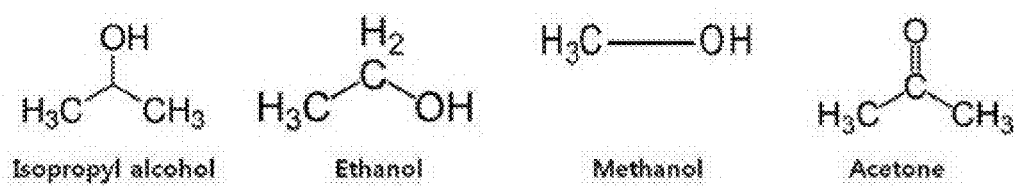
FIG. 20A is structural formulas of isopropyl alcohol, ethanol, methanol and acetone.
FIG. 20B is a particle distribution graph of marker-including liposome solutions after lyophilization and rehydration in the process of preparing a frozen powder of marker-including liposomes.
Figure 20:
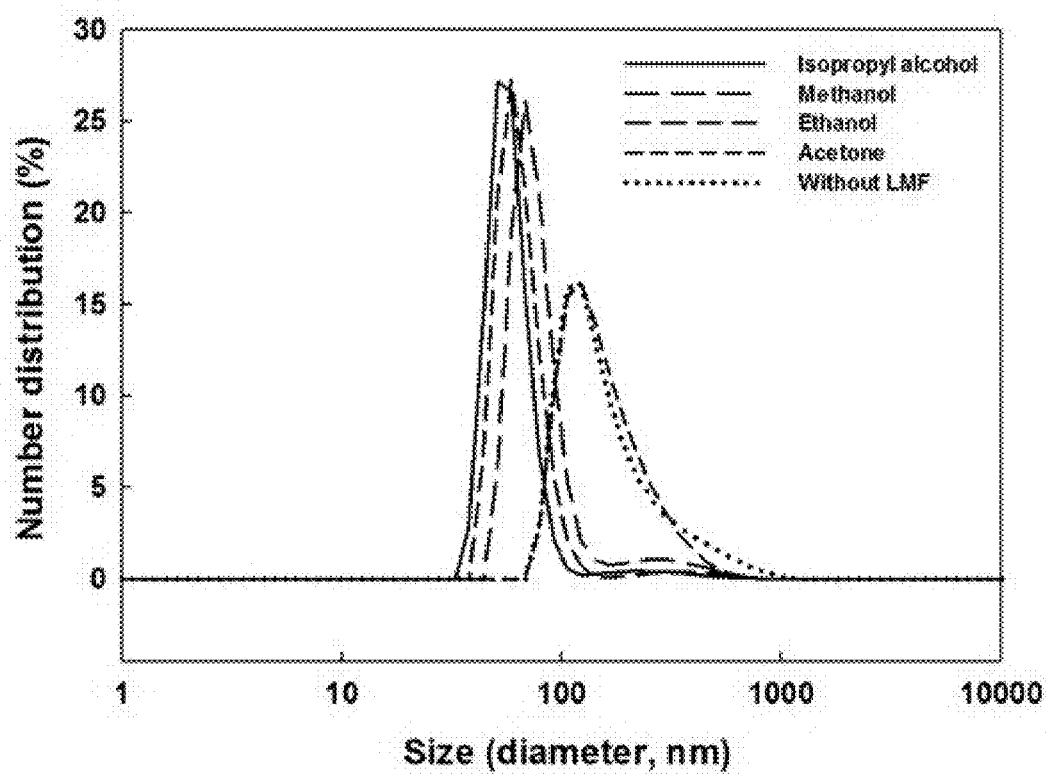

DLS analysis results showed that, as shown in FIG. 20B, when ethanol and methanol were used for the container, the distribution was similar to when the isopropyl alcohol container was used. Upon rehydration after lyophilization, the marker-including liposome structure was neither destroyed nor expanded and its shape was well maintained. However, acetone, which has a melting point midway between isopropyl alcohol and methanol, showed the same results as when the isopropyl alcohol container was not used.

FIG. 20A is structural formulas of isopropyl alcohol, ethanol, methanol and acetone, and FIG. 20B is a particle distribution graph of the marker-including liposome solutions after lyophilization and rehydration in the process of preparing a frozen powder of marker-including liposomes.

The invention claimed is:

1. A method of preparing a lyophilized liposome powder comprising:
 a) preparing a liposome composition comprised of a phospholipid and a cryoprotectant by a process comprising:
  mixing a phospholipid solution with a cryoprotectant solution to produce an inverted micelle solution, wherein the phospholipid is dissolved in a mixed organic solvent of ethyl acetate and n-hexane in a ratio of 4:1, and the cryoprotectant is dissolved in distilled water,
  mixing the inverted micelle solution with a cryoprotectant solution to produce a double emulsion solution, wherein the cryoprotectant is dissolved in distilled water, and
  stirring the double emulsion solution to evaporate the organic solvent present between lipid bilayers in the double emulsion and produce the liposome composition, and
 b) lyophilizing the liposome composition by placing a container containing the liposome composition, in a container containing a liquid selected from the group consisting of isopropyl alcohol, ethanol and methanol, followed by freeze drying at 80° C., wherein the liposome container is immersed in the liquid during lyophilization.

2. The method according to claim 1, wherein the cryoprotectant comprises one or more selected from trehalose and sucrose.

3. The method according to claim 1, wherein the liposome composition comprises one or more selected from a compound, a microorganism, a protein and an enzyme.

4. The method according to claim 3, wherein the compound is a pharmaceutical active ingredient or a functional health ingredient.

* * * * *

UNITED STATES PATENT AND TRADEMARK OFFICE
CERTIFICATE OF CORRECTION

PATENT NO. : 10,660,853 B2  
APPLICATION NO. : 15/760894  
DATED : May 26, 2020  
INVENTOR(S) : Chang et al.

Page 1 of 1

It is certified that error appears in the above-identified patent and that said Letters Patent is hereby corrected as shown below:

In the Claims

Claim 1, Column 14, Line 41:
"freeze drying at 80° C., wherein"
Should be deleted and replaced with:
-- freeze drying at -80° C., wherein --

Signed and Sealed this
Eighth Day of September, 2020

Andrei Iancu
*Director of the United States Patent and Trademark Office*